United States Patent
Gulino et al.

(10) Patent No.: US 9,758,598 B2
(45) Date of Patent: Sep. 12, 2017

(54) METHOD FOR PREPARING A HYDROGEL MATRIX BY PHOTOPOLYMERIZATION

(75) Inventors: Danielle Gulino, Lumbin (FR); Abbas Mgharbel, Grenoble (FR); Alice Nicolas, Saint-Egrève (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 36 days.

(21) Appl. No.: 14/359,425

(22) PCT Filed: Aug. 29, 2012
(Under 37 CFR 1.47)

(86) PCT No.: PCT/EP2012/066781
§ 371 (c)(1),
(2), (4) Date: Jul. 27, 2015

(87) PCT Pub. No.: WO2013/079231
PCT Pub. Date: Jun. 6, 2013

(65) Prior Publication Data
US 2016/0002368 A1    Jan. 7, 2016

(30) Foreign Application Priority Data
Nov. 28, 2011 (FR) .................................. 11 60874

(51) Int. Cl.
| | |
|---|---|
| *C08F 2/48* | (2006.01) |
| *C08F 120/56* | (2006.01) |
| *C08F 220/56* | (2006.01) |
| *C12N 11/08* | (2006.01) |
| *G03F 7/20* | (2006.01) |

(52) U.S. Cl.
CPC .............. *C08F 2/48* (2013.01); *C08F 120/56* (2013.01); *C08F 220/56* (2013.01); *C12N 11/08* (2013.01); *G03F 7/20* (2013.01)

(58) Field of Classification Search
CPC ........................................................ C08F 2/48
See application file for complete search history.

(56) References Cited

PUBLICATIONS

IRGACURE 819 data sheet, 2001, pp. 1-3.*
Ruan et al. J of Applied Polymer Science, 2006, 101:1181-1187.*
Kloxin, A., et al., "In situ elasticity modulation with dynamic substrates to direct cell phenotype", "Biomaterials", Sep. 27, 2009, pp. 1-8, vol. 31.
Lo, C., et al., "Cell Movement is Guided by the Rigidity of the Substrate", "Biophysical Journal", Jul. 2000, pp. 144-152, vol. 79, No. 1.
Tse, J., et al., "Preparation of Hydrogel Substrates with Tunable Mechanical Properties", "Current Protocols in Cell Biology", Jun. 2010, pp. 1-16, Supplement 47, vol. 10, No. 16.
Tse, J., et al., "Stiffness Gradients Mimicking In Vivo Tissue Variation Regulate Mesenchymal Stem Cell Fate", "PLoS One", Jan. 5, 2011, pp. e15978, 1-10, vol. 6, No. 1.
Wong, J., et al., "Directed Movement of Vascular Smooth Muscle Cells on Gradient-Compliant Hydrogels", "Langmuir", Jan. 9, 2003, pp. 1908-1913, vol. 19.
Zaari, N., et al., "Photopolymerization in Microfluidic Gradient Generators: Microscale Control of Substrate Compliance to Manipulate Cell Response", "Advanced Materials", Dec. 17, 2004, pp. 2133-2137, vol. 16, No. 23-24.

* cited by examiner

*Primary Examiner* — Bin Shen
(74) *Attorney, Agent, or Firm* — Hultquist, PLLC; Mary B. Grant

(57) ABSTRACT

The invention relates to a method for preparing a hydrogel type matrix comprising at least two contiguous zones with distinct stiffnesses, comprising a step to photopolymerize a solution comprising one or several polymerizable compounds and a photopolymerization initiator, by application of light onto the entire solution and at a different intensity in at least two zones of the solution, as a result of which a hydrogel matrix is obtained comprising at least two contiguous zones with distinct stiffnesses, characterized in that the photopolymerization step is done in the presence of a polymerization catalyst.

12 Claims, 8 Drawing Sheets

METHOD FOR PREPARING A HYDROGEL MATRIX BY PHOTOPOLYMERIZATION

CROSS-REFERENCE TO RELATED APPLICATIONS

This application is a U.S. national phase under the provisions of 35 U.S.C. §371 of International Patent Application No. PCT/EP12/66781 filed Aug. 29, 2012, which in turn claims priority of French Patent Application No. 1160874 filed Nov. 28, 2011. The disclosures of such international patent application and French priority patent application are hereby incorporated herein by reference in their respective entireties, for all purposes.

TECHNICAL DOMAIN

This invention relates to a method for preparing a hydrogel matrix by photopolymerization, this matrix possibly being characterized by distinct contiguous zones that can have a stiffness gradient of the order of 1 kPa/µm and a stiffness of between 100 Pa and 500 kPa.

This method may be applied for the design of matrices for use for cell discrimination, particularly healthy and cancer cells.

It is known that cells interact with their cellular or matrix environment.

Three essential factors affect cell survival through their bonding, migration and proliferation capabilities:
geometric constraints;
the chemical environment; and
the mechanical environment, such as the action of external forces or stresses, mechanical properties of the matrix with which the cells are in contact.

In particular, since the work by Lo et al. (Biophys. J., 79, 144-152), it has been confirmed that cells are sensitive to the elastic properties of the matrix on which they are located. For each cell type, there is a minimum stiffness threshold below which the cell cannot bond despite a favorable surface chemistry. Above this threshold, the cells bond and survive. In particular, it has been observed that isolated cells migrate towards the zones in the matrix in which the stiffness is high, this effect being more marked when the stiffness of the matrix is similar to the threshold stiffness of the cell type considered. However, the response of cancer cells to the stiffness is different from the response of healthy cells.

Based on the observation mentioned above, it seems quite possible to localize, provide guidance and/or make a cell sort with matrices (or substrates) that have spatially modulated mechanical properties (by means of different zones with distinct stiffnesses) and uniform surface chemical properties.

Matrices satisfying these criteria may be hydrogel type polymer matrices with a juxtaposition of zones with different stiffnesses. This type of matrix has several advantages:
preparation of this type of matrix can be simpler than the preparation of chemical chips;
the material from which these matrices are formed is characterized by long life (particularly no degradation over approximately a month);
the possibility of selective surface functionalization coupled with stiffness patterns.

Different attempts to produce hydrogel type matrices with juxtaposition of zones with different stiffnesses have been disclosed in prior art, particularly by solution photopolymerization.

Thus, some authors have used microfluidics tools to produce a gradient of constituents to be cross-linked, thus restricting the photopolymerization technique to practical interest alone but without any technological interest. Stiffness gradients (of the order of 1 kPa/mm in the best case) are limited by microfluidics and not by photopolymerization.

Other authors have chosen to photopolymerize a uniform solution through a stencil, particularly as described in the document written by Tse et al. (Curr. Protoc. Cell. Biol. 10.16.1-10.16.16, June 2010), the properties of the solution used and the operating conditions being such that a polymerization time of the order of one minute and a stiffness gradient of the order of one kPa/mm can be obtained. With such a polymerization time, the chemical species in the solution diffuse easily from one zone to another during the polymerization process, which reduces resolution of the zones formed and furthermore, generates stiffness uniformity by diffusion of material between the more illuminated zones and the less illuminated zones during photopolymerization.

Considering the existing situation in the field of preparation of matrices mentioned above, the authors of this invention set themselves the goal of developing a method for preparation of a polymeric matrix with zones (or patterns) with distinct stiffnesses, to obtain zones with distinct stiffnesses with polymerization times shorter than times obtained in prior art, the stiffness gradient between two contiguous zones possibly being of the order of one kPa/µm.

PRESENTATION OF THE INVENTION

The authors discovered surprisingly that if a combination of specific ingredients is used in the polymeric solution, matrices with the advantages mentioned above can be obtained.

Thus, the invention relates to a method for preparing a hydrogel type matrix comprising at least two contiguous zones with distinct stiffnesses, said method comprising a step to polymerize a solution comprising one or several polymerizable compounds and a photopolymerization initiator, by application of light onto the entire solution and at a different intensity in at least two zones of the solution, as a result of which a hydrogel matrix is obtained comprising at least two contiguous zones with distinct stiffnesses, characterized in that the photopolymerization step is done in the presence of a polymerization catalyst.

By varying the combined use of a photopolymerization initiator and a polymerization catalyst in the solution containing the polymerizable compound(s), and thus the initiated photopolymerization technique, the polymerization time obtained (possibly of the order of one second) is very much shorter than in the case in which polymerization is induced only by the simple use of a photopolymerization initiator.

This property (namely a shorter photopolymerization time) results in the following advantages:
limitation of the reagent diffusion phenomenon (monomers, initiator and catalyst) from one zone to another during the photopolymerization process, which finally gives distinct stiffness zones with better resolution;
the possibility of obtaining narrow and contiguous zones with distinct stiffnesses with a very steep stiffness gradient between two zones (for example of the order of one kPa/µm), by varying the spatial modulation of the intensity at the scale of the width of the zone to be obtained (for example of the order of 1 µm).

As mentioned above, the method according to the invention uses a solution comprising one or several polymerizable compounds, a photopolymerization initiator and a polymerization catalyst, although the solution may contain other ingredients.

It should be understood that the polymerizable compound(s) used is (are) precursor compounds of the hydrogel material that will form the matrix, namely a gel type material obtained in an aqueous medium, for example these hydrogel materials may be:
- polyacrylamides;
- polyethyleneglycols containing repetitive patterns derived from polymerization of acrylate or methacrylate compounds;
- polysaccharides, possibly modified (for example modified polysaccharides containing repetitive patterns derived from polymerization of acrylate compounds);
- (co)polymers derived from polymerization of diacrylate and/or (meth)acrylate compounds;
- polyvinyl alcohols containing repetitive patterns derived from polymerization of acrylate or methacrylate compounds;
- dextranes containing repetitive patterns derived from polymerization of (meth)acrylate compounds;
- polypropylene fumarates and derivatives of them, such as poly(propylene-co-ethyleneglycol fumarate); and
- combinations of these materials.

The polymerizable compound(s) may be monomers or oligomers or polymers comprising at least one polymerizable function.

The polymerizable compounds used can thus be:
acrylamide monomers to obtain polyacrylamides;
acrylate and/or methacrylate compounds put in the presence of polyethyleneglycols to obtain polyethyleneglycols comprising repetitive patterns derived from polymerization of acrylate and/or methacrylate compounds, the polymerizable function being located at these acrylate and/or methacrylate compounds;
acrylate monomers (that will be put in the presence of polysaccharide compounds) to obtain polysaccharides modified by acrylate compounds;
diacrylate and/or (meth)acrylate monomers to obtain (co) polymers derived from the polymerization of diacrylate and/or (meth)acrylate compounds;
polyvinyl alcohols put in the presence of acrylate and/or methacrylate compounds to obtain polyvinyl alcohols containing repetitive patterns derived from the polymerization of acrylate or methacrylate compounds of polyvinyl alcohols, the polymerizable function being located at these acrylate and/or methacrylate compounds;
(meth)acrylate monomers put in the presence of dextrane compounds, to obtain dextranes containing repetitive patterns derived from polymerization of (meth)acrylate compounds;
propylene fumarate monomers, to obtain polypropylene fumarates and derivatives of them.

Photopolymerization initiators that can be used may be initiators of the aromatic ketones family, acridine compounds, fluorone compounds.

Examples of aromatic ketones include:
benzyl ketals, such as ketals satisfying the following formula:

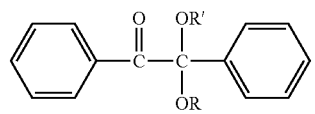

in which R and R' may represent an alkyl group;
benzoin compounds;
α-aminoaromatic ketones;
phosphine compounds;
benzophenone compounds;
thioxanthone.

Phosphine compounds include compounds sold under the name Irgacure, such as Irgacure 819® with the following formula:

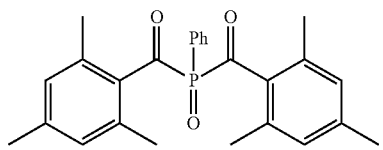

Ph denotes a phenyl group.

Polymerization catalysts that are responsible for the high acceleration of the photopolymerization reaction rate are advantageously amine compounds.

A primary amine or secondary amine type compound might be sufficient when the photopolymerization initiator has strong reactivity to one or more of the polymerizable compounds present in the solution. In this case, the amine compound reacts with a photopolymerization initiator to form a free radical that reacts with oxygen through a peroxidation reaction, the amine compound thus being considered to play the indirect role of oxygen trap (which is a hindrance to a radical chain reaction).

When the efficiency of the photopolymerization initiator towards the polymerizable compound(s) is poor, the amine compound may be a reactional intermediary between the photopolymerization initiator and the polymerizable compound(s), thus performing a catalyst role. In this case, the amine compound is advantageously a compound of the tertiary amine type.

One example of an amine compound that can perform the role of a polymerization catalyst is n-propylamine.

Apart from the above-mentioned ingredients (monomer(s), initiator and catalyst), the solution may include:
- stains (such as methylene blue) so as to adjust the wavelength of the lamp of the photopolymerization initiator;
- cross-linking agents;
- water, preferably deionized; and
- mixes of these ingredients.

Cross-linking agents include monomers comprising at least two polymerizable functions, for example bisacrylamide monomers, such as N,N'-methylenebis-acrylamide.

For example, the solution may comprise acrylamide, a photopolymerization initiator with the following formula:

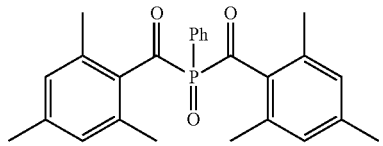

where Ph denotes a phenyl group,
n-propylamine as the polymerization catalyst, N,N'-methylenebisacrylamide as the cross-linking agent and water.

As mentioned above, light is applied to the entire solution (to generate photopolymerization of the entire solution in hydrogel) and at a different intensity at at least two contiguous zones of the solution, as a result of which a hydrogel matrix is produced comprising at least two contiguous zones with distinct stiffnesses.

In other words, this means that light is applied, for example UV light and more specifically UV-A light, to the solution following a distribution with spatially modulated intensity, so as to access the required distribution of contiguous zones with different stiffnesses (knowing that the applied light intensity has an influence on the cross-linking rate of the hydrogel and therefore its stiffness).

The spatially modulated intensity distribution may be obtained by:

(i) use of a stencil above the solution to be treated, for example a stencil comprising one or several grey levels, the opaqueness of which reflects the required cross-linking rate; or (ii) a light source, the intensity of which is spatially modulated by an interference grating, a diffraction grating or a holographic pattern.

When a stencil is used, the material from which the stencil is made is chosen as a function of:

(i) absorption of the absorbent material within the range of wavelengths of the lamp used during photopolymerization;

(ii) resolution of the required zones (or patterns).

When it is required to make submicronic sized patterns, the stencil may consist of:

- a glass or quartz substrate covered with metal or metallic oxide layers according to an arrangement suitable for obtaining the required patterns;
- a liquid crystal substrate;
- a thermoplastic material substrate (such as a polymethacrylate, a polycarbonate, a polystyrene) obtained by thermomolding or ion etching.

When the objective is to make patterns with a size of 10 μm or larger, the stencil may consist of a plastic film treated by laser printing, or an assembly of opaque or reflecting films.

When the objective is to make more complex patterns, modulations with more complex intensity than simple binary modulations should be used through the use of a stencil comprising a distribution of grey levels necessary to obtain the required patterns. This type of stencil may consist of a glass or quartz plate covered on one face by a metallic layer (for example chromium) that is lithographed and/or etched so as to create different grey levels.

Preferably, light is applied onto the solution through a stencil so as to delimit zones with distinct light intensity.

In this case, the method according to the invention may include a step prior to preparation of the stencil.

Depending on the required hydrogel matrix, those skilled in the art may decide to perform preliminary operations before performing the photopolymerization step as such.

The following preliminary operations may be performed:

(i) the choice of component ingredients of the solution such as polymerizable compounds (the choice of which will be fixed by the hydrogel material to be obtained), the photopolymerization initiator that can be selected as a function of the wavelength of the light source and the spatial resolution of the required stiffness patterns, and the polymerization catalyst that can depend on the nature of the photopolymerization initiator;

(ii) the evaluation of the threshold duration to polymerize the solution by the light source, knowing that as the required stiffness gradient increases (for example, 1 kPa/μm), the threshold duration must decrease (for example of the order of one second), which can make it necessary to adapt the concentration of initiator and/or catalyst to accelerate or slow down the photopolymerization reaction as a function of the required stiffness gradient;

(iii) characterization of the stiffness as a function of the transmitted power and the duration for a homogeneous illumination that may form a benchmark for the choice of light application parameters during photopolymerization (these parameters may also be qualified as illumination parameters);

(iv) starting from the above-mentioned characterization, selection of the illumination contrast between rigid patterns and so-called "soft" patterns (in comparison with rigid patterns), this selection possibly passing through the choice of grey levels for stencils, the choice of the intensity gradient for holographic patterns.

Photopolymerization is advantageously done in an inert atmosphere (for example hydrogen or argon) so as to avoid the presence of oxygen that inhibits the polymerization reaction. It is thus possible to degas the solution so as to eliminate oxygen present in this solution, in addition to working in an inert atmosphere.

Photopolymerization is conventionally done at a temperature at which the solution remains liquid, namely at a temperature conventionally varying from 0 to 100° C.

As mentioned above, the matrices prepared using the method according to the invention may be characterized by at least two contiguous zones with distinct stiffnesses with a stiffness gradient of more than 30 Pa/μm, more specifically a stiffness gradient of the order of 1 kPa/μm, or even more specifically a gradient equal to 1 kPa/μm, and advantageously a stiffness between 100 Pa and 500 kPa and advantageously a zone width of the order of 1 μm.

More specifically, one of said two contiguous zones with the highest stiffness is in the form of a pattern with dimensions smaller than 100 μm.

Matrices of this type may be made of a hydrogel originating from polymerization of acrylamide and N,N'-methylenebisacrylamide.

Since these matrices can enable sudden stiffness changes of several kPa on a scale smaller than the size of a biological cell, it is quite natural that these matrices will be applied in a cell adhesion method, this method possibly being aimed at confinement of cells, sorting of cells, positioning of cells and more specifically positioning of cells and controlling the cellular geometry, deformation of cells. Consequently, these matrices may be used as diagnostic tools for the determination of target organs of metastatic cells, cells having a different response to the stiffness depending on the cell type.

To achieve this, before they can be used for these applications, matrices may need to be subjected to a matrix functionalization step at the end of the preparation method after the photopolymerization step, using a protein inducing cell adhesion through integrins, such a protein possibly being fibronectin, collagen, laminin or RGD type peptides.

The invention may also relate to an in vitro cell adhesion method comprising:

a) a step to use the hydrogel type matrix preparation method as defined above;

b) a step in which cells of one or several types are deposited on the matrix obtained in step a), as a result of which the cells of at least one of the types mentioned above adhere entirely or partly to some zones of the matrix with higher stiffness than contiguous zones.

This adhesion method may be aimed at:
positioning cells on specific zones;
more specifically, positioning on specific zones and controlling the cellular geometry, which is equivalent to stating that the method deals with the shaping of cells; and
deforming the cells.

More specifically, the invention may thus relate to an in vitro cell shaping method comprising:

a) a step to use the hydrogel type matrix preparation method as defined above;

b) a step to deposit cells of one or several types on the matrix obtained in step a), as a result of which the cells of at least one of the types mentioned above are concentrated entirely or partly on some zones of the matrix with higher stiffness than contiguous zones and adopt the shape of said higher stiffness zones.

The zones with higher stiffness than their contiguous zones are qualified below as patterns, these patterns forming cell attraction zones.

Cell adhesion refers conventionally to total or partial cell positioning on said zones, which does not mean that these cells cannot be mobile within said zones, particularly in the case in which these zones have a stiffness gradient.

Concerning the positioning of cells in general, with matrices obtained using the method according to the invention, it may be possible to position cells, for example epithelial, endothelial, fibroblastic, astrocyte or muscular type cells, these cells having the special feature of migrating towards zones with the highest stiffness. For example, it might be possible to design matrices with stiffness zones organized so as to form cell pathways, for example channels with a stiffness greater than zones adjacent to these channels, thus enabling a concentration of cells in these channels. Furthermore, if a stiffness gradient is planned inside the channels, the cells will migrate towards increasing stiffness.

It might also be possible to design matrices containing zones with higher stiffness (these zones possibly being qualified as patterns) than the zones surrounding the patterns, these patterns having at least one cell dimension (for example less than 100 µm and more specifically of the order of 10 to 100 µm depending on the cell type) and furthermore, these patterns being spaced so as to:

(i) limit the number of cells present on the zones surrounding the patterns, these zones having a lower stiffness than said patterns; and (ii) prevent the cells from being shared among several patterns.

For example, for REF52 and HUVEC type cells, a space varying from 80 to 200 µm between the patterns may be sufficient to satisfy conditions (i) and (ii) mentioned above.

Concerning positioning of cells and controlling the cell geometry, due to the stiffness gradients, matrices obtained by the method according to the invention may allow migration of cells towards zones with higher stiffness and conferring shapes of specific patterns onto these zones, conformation of the shape of the cells thus positioned to the shape of the patterns of said zones, these patterns having at least one dimension of the order of the same scale as a cell (for example a dimension varying from 10 to 100 µm depending on the cell type), so as to enable confinement under identical geometric and mechanical conditions. In particular, it may be possible to create a matrix reproducing a set of conditions similar to adhesion conditions found in vivo in tissues or embryos.

Consequently, positioning of a large quantity of cells isolated or in aggregates with controlled sizes under identical geometric and mechanical conditions and particularly under geometric and mechanical conditions similar to those encountered in the tissues of the organism, may be a good tool for testing the impact of molecules of interest that might act on cell functions, because it enables a statistical analysis on a large population in a single experiment. For example, the analysis may apply to the analysis of cell polarity relative to administration of molecules of interest, for example polarity in an epithelial tissue with consequences on the integrity of the tissue (a defect in the basolateral polarity of renal cells that can cause the formation of cysts and renal fibrosis) or an impact on morphogenesis, extension of embryo tissues being made along the long direction of the cells. Knowing the impact of the molecule of interest on the cell polarity or conversely the impact of cell polarity on the efficiency of the molecule of interest, are found to be crucial parameters for evaluating the efficiency of the molecule of interest or its potential undesirable effects. More generally, it is possible to test the impact of the molecule of interest on cell spreading, organization of the cytoskeleton, whether or not cell sensitivity to the mechanical properties of the substrate is maintained, associated with dysfunction of cell adhesion. Conversely, the impact of the position of the centrosome, the Golgi apparatus and the core (controlled by the geometric stress) and cell contractibility (controlled by the elasticity of the extracellular matrix) on the effect of the molecule of interest can be tested.

Concerning cell deformation, matrices obtained using the method according to the invention make it possible to substantially deform cells. For example, it could be envisaged to design matrices comprising higher stiffness zones than zones contiguous to said zones. More specifically, the matrix may have a set of patterns with a higher stiffness than the zones surrounding said patterns. Advantageously, these patterns have at least one dimension smaller than the scale of the cell (for example a dimension varying from 0.5 to 10 µm) and are advantageously spaced to enable spreading of cells on several patterns, this spreading being the cause of cell deformation. Functionally, focal adhesion and the associated stress fibers are more likely to occur on zones with higher stiffness and focal complexes and the associated entangled actin filaments are more likely to occur on zones with lower stiffness.

Concerning sorting of cells, matrices obtained using the method according to the invention can make a sort, for example between glial cells and neurons. Glial cells are the mechanical and chemical support for the growth of neurons in the brain. At the present time, in vitro studies on primary neurons are limited by the difficulty of managing the presence of glial cells. The presence of these cells makes it possible to reproduce a chemical environment similar to in vivo conditions, but makes spatial organization of neurons very difficult because they grow on the glial cell carpet. Knowing that glial cells do not grow on substrates with low stiffness, with matrices with stiff zones and stiffer zones it could be envisaged to make a concomitant culture of neurons and glial cells with segregation of these two types of cells, as a result of which a network of "pure" neurons can be organized in a chemical environment of glial cells.

The cell sort may also be based on mobility of cells within zones with higher stiffness, the less mobile cells moving less within said higher stiffness zones.

Concerning the determination of target organs of metastatic cells, it is known that some tumors disseminate metastatic cells in remote organs, such as the breast or lung tumors that disseminate cells into the lungs, kidneys, bones or brain. Knowing that cancer cell proliferation and migration rates are maximum in zones of matrices with stiffness corresponding to that of the invention, it might be possible to envisage designing matrices containing stiffness bands chosen as a function of the expected phenotypes using the method according to the invention (the dominant cell phenotype in each band being the phenotype targeting the organ that has the same stiffness).

Matrices according to the invention can be incorporated into devices capable of receiving cells, more particularly eucaryote cells, preferably mammal cells and even more preferably human cells, said devices comprising a matrix like that defined above and obtained by the method as defined above.

The invention will now be described with reference to an example embodiment of the method according to the invention, this example being provided for illustrative purposes of the invention and not in any way forming a limitation.

DETAILED PRESENTATION OF PARTICULAR EMBODIMENTS

Example 1

This example illustrates the preparation of a hydrogel matrix comprising two zones with different stiffnesses involving the following steps:
  a step to prepare a glass cover glass that will be used as a support for the hydrogel matrix (a);
  a step in which a stencil is prepared (b);
  a step in which the hydrogel matrix is prepared (c).

a) Preparation of the Cover Glass

A bottom cover glass is cleaned with a 0.1 mol/L soda solution for 10 minutes. It is then rinsed intensively with water and then ethanol. It is then immersed for 5 minutes in a 10% solution of APTMS (3-aminopropyltrimethoxysilane) in ethanol (5 ml APTMS for 45 mL ethanol), while stirring slowly. The cover glass is then rinsed with ethanol and kept for 10 minutes while stirring slowly in an ethanol bath. After simple rinsing with de-ionized water, the cover glass is immersed in a 0.5% glutaraldehyde solution in water for 25 minutes. It is then rinsed intensively with water and strongly dried. The result obtained is a cover glass with aldehyde functions on its surface, which will enable covalent grafting of hydrogel in polyacrylamide, which will be prepared subsequently.

b) Preparation of a Stencil

An optical microscopy slide (26 mm×76 mm) is washed in a solution of oxygenated water/concentrated sulfuric acid in proportion 1:1, for 20 minutes. A cleaved silicon wafer is fixed onto the left half of the slide. This wafer hides the transparent part before the deposit is made. 1 nm of titanium and then 4 nm of chromium are deposited by a Plassys type electron gun evaporator.

The slide is then made hydrophobic by an Optool treatment (Daikin DSX): immersion for 1 minute in Optool diluted to 1:1000 in perfluorohexane. The slide is then left for 1 hour in steam at 80° C. It is finally immersed in perfluorohexane for 10 minutes while stirring slowly.

Figure 1:
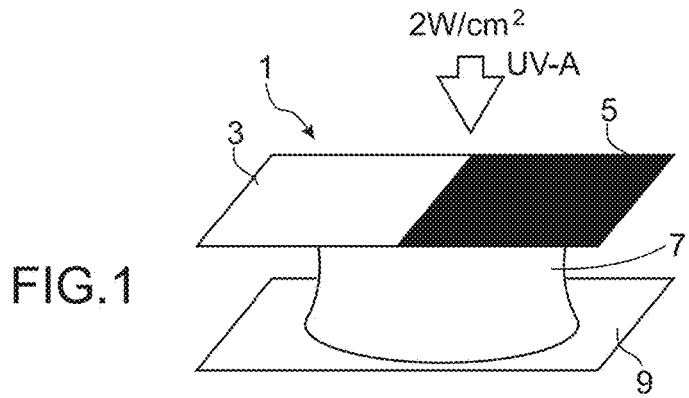
FIG. 1 shows a view of the device used for example 1.

The slide obtained is shown in FIG. 1 as reference 1, this slide comprising two zones:
  a transparent zone 3;
  a zone 5 covered with a 5 nm layer (1 nm of titanium and 4 nm of chromium) (called the grey level zone) contiguous with the transparent zone,
  this slide forming a stencil that will be inserted between a light flux (shown by an arrow in the figure indicating that it is a UV-A flux at 2 W/cm$^2$) and the solution (shown as reference 7) deposited on the glass slide 9 mentioned above and that will be photocrosslinked in order to form the target matrix, namely a matrix with two contiguous zones with distinct stiffness, these zones corresponding to the geometry of the stencil.

A second stencil is prepared in the same way as defined above, except that the so-called grey level zone is composed of a 1 nm layer of titanium on which 19 nm of chromium is deposited.

c) Preparation of the Hydrogel Matrix

Irgacure 819® (1.7 mg) is weighed in a flask opaque to ultraviolet rays. n-propylamine (10 µL) is added. The mixture is heated for 2 minutes at 50° C. After heating, the result obtained is a homogeneous and transparent solution. De-ionized water (490 μL), acrylamide (250 μL of a 40% solution) and N,N'-methylenebisacrylamide (250 μL of a 2% solution) are added. The complete mixture is homogenized gently with a pipette, to limit incorporation of oxygen.

30 μL of the solution obtained is placed on the 30 mm glass cover glass prepared according to the protocol described above. The cover glass is placed on a sample holder on which shims are placed to maintain a space of 40 μm between the cover glass and the previously prepared stencil deposited on the shims.

The assembly (stencil, solution, cover glass) is illuminated by an Eleco UVP281 fiber lamp (2 W/cm$^2$) for 20 seconds, as shown in FIG. 1. This assembly is then immersed in water to detach the stencil from the hydrogel matrix thus formed using pliers. The hydrogel matrix is rinsed 3 times with de-ionized water.

Two tests were carried out using the same methods:
a first test with the stencil comprising a grey level zone (composed of a layer composed of 1 nm of titanium and 4 nm of chromium); and
a second test with a stencil comprising a grey level zone (composed of a layer of 1 nm of titanium and 19 nm of chromium).

The surface topography and the stiffness of the matrix obtained were determined for both tests.

Figure 2A:
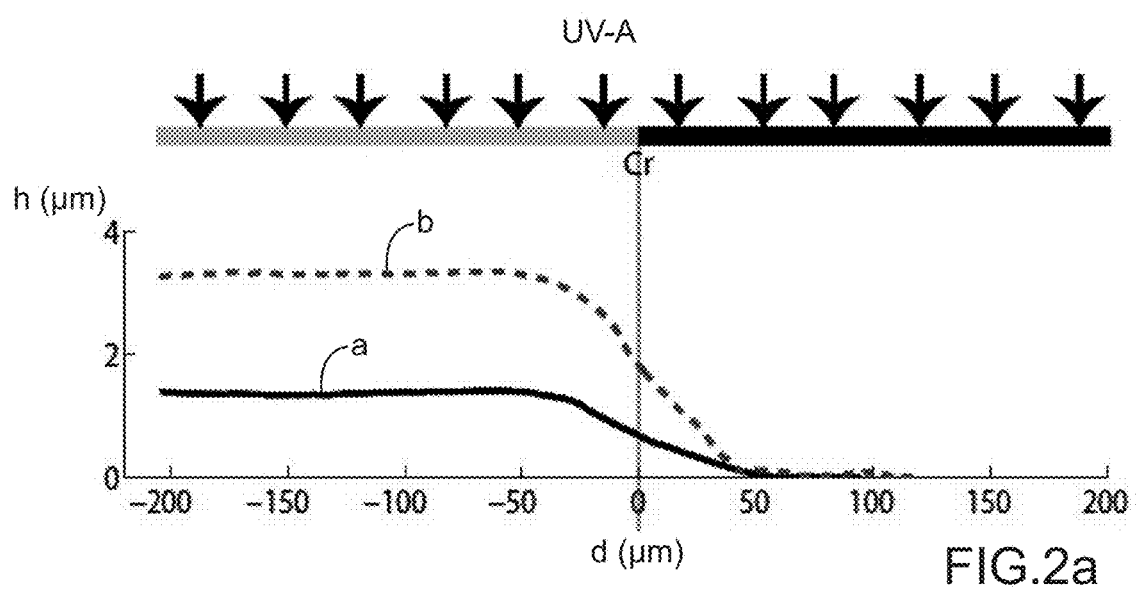
FIG. 2a shows a chart illustrating the variation in the height h (in µm) of the matrix obtained for example 1 as a function of the distance d (in µm) (0 corresponding to the delimitation between the zone illuminated through the transparent zone of the stencil and the zone illuminated through the grey level zone).

The surface topography was determined by measuring the height of the matrix as a function of the distance d relative to the delimitation between the zone illuminated through the transparent zone (this delimitation being equal to 0 at the abscissa) and the zone illuminated through the grey level zone of the stencil, the results being shown in FIG. 2a that shows the variation in the height h (in μm) as a function of the distance d (in μm), this distance being defined in the upper part of the graph by the representation of zones of the stencil through which the illumination was made.

A substantial reduction in the height of the matrix is observed both for the first test (curve a) and for the second test (curve b), when moving from the zone illuminated through the transparent zone of the stencil to the zone illuminated through the grey level zone of the stencil.

The stiffness of the matrix obtained was determined by measuring the local stiffness of the hydrogel by atomic force microscopy (AFM) in aqueous medium (brand JPK). The resistance of the matrix to penetration of a point is recorded. A 400 μm scan is made through the boundary. The scans are made at a pitch of 10 μm. The result is a series of indentation curves. Each curve is processed using the manufacturer's protocol with an elastic indentation model. Each point on the graph is the average of 3 measurements made on 3 points at a spacing of 10 μm along a direction parallel to the boundary.

Figure 2B:
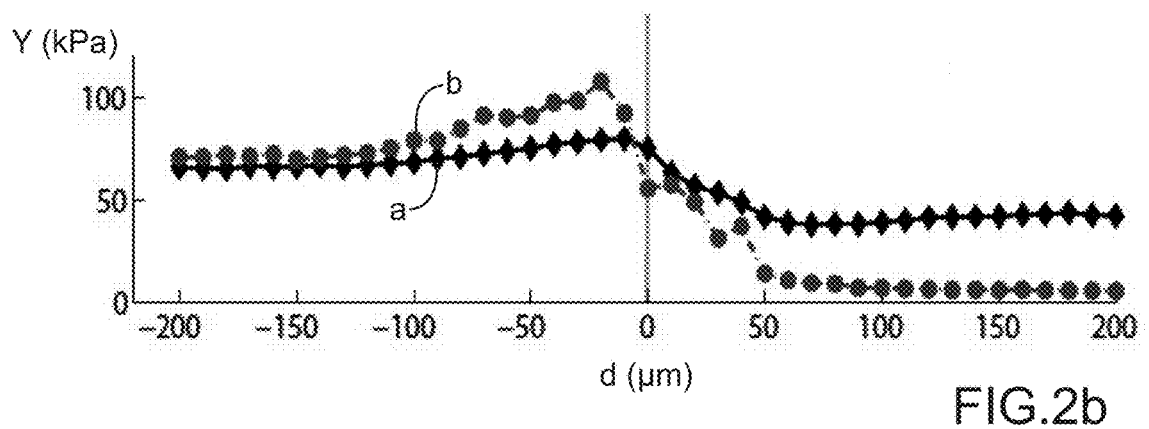
FIG. 2b shows a chart illustrating the variation of the stiffness Y (in kPa) of the matrix obtained for example 1 as a function of the distance d (in µm) (0 corresponding to the delimitation between the zone illuminated through the transparent zone of the stencil and the zone illuminated through the grey level zone).

The results are shown in FIG. 2b representing the variation of the stiffness Y (in kPa) as a function of the distance d (in μm) relative to the delimitation between the zone illuminated through the transparent zone (this delimitation being equal to the value 0 at the abscissa) and the zone illuminated through the grey level zone of the stencil.

It is found that there is a substantial reduction in the stiffness both for the first test (curve a) and the second test (curve b) when moving from the zone illuminated through the transparent zone of the stencil (this illuminated zone can be qualified as a stiff zone) to the zone illuminated through the grey level zone of the stencil (this illuminated zone can be qualified as a soft zone), the stiffness gradient being of the order of 1 kPa/μm, particularly for the second test.

A cell culture was also made on the matrices obtained above.

Before starting, the matrix was functionalized with fibronectin. This was done by gluing the 30 mm diameter cover glass on which the hydrogel is polymerized to the bottom of a Petri dish in which a 35 mm diameter hole is drilled. Water is drawn out of the dish, 1 mg of Sulfo SDA (Pierce) (corresponding to succinimidyl-ester diazirine) is dissolved in 2.27 mL of sterile de-ionized water. The solution obtained is deposited on the matrix and is left for 2 hours in the dark. After this time, it is drawn in with the pipette and 2 mL of a 25 mg/mL fibronectin solution in sterile PBS is deposited for 1 hour. The dish is always kept in the dark. This solution is drawn in with the pipette and the dish is placed under the Eleco UVP281 lamp (2 W/cm$^2$) for 3 min. The matrix is rinsed 3 times with sterile PBS (phosphate buffer salt).

HUVEC cells (that correspond to mature human endothelial cells isolated from the umbilical cord vein) are seeded at a density of 2000 cells/cm$^2$ in medium M199, 20% FCS (foetal calf serum), 2% LSGS (low serum growth supplement), 1% ATAM (antibiotics (penicillin, streptomycin)+antimycotic, Invitrogen).

Figure 2C:
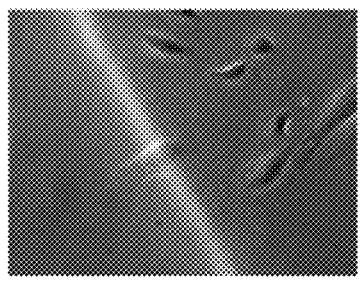
FIG. 2c shows a photograph of the matrix obtained for the example 1 after cell seeding.

As can be seen in FIG. 2c which is a photograph taken by phase contrast microscopy, with 20× magnification on an inverted microscope 24 hours after seeding, there is a crossing of a delimitation cell between the soft zone and the stiff zone.

The topographic profile does not influence the cell organization. Cells pass through the stiffness boundary by positioning themselves perpendicular to the boundary (as shown in FIG. 2c). If topography were to affect cell behavior, the cells should align themselves along the boundary, which is obviously not the case.

Example 2

This example illustrates the preparation of a matrix comprising zones with distinct stiffness in the form of 10 μm lines alternated with 40 μm lines involving the following steps:
a step to prepare a glass cover glass that will be used as a support for the matrix (a);
a step in which a stencil is prepared (b);
a step in which the hydrogel matrix is prepared (c).

a) Preparation of the Cover Glass

The cover glass is prepared in the same way as in example 1 described above.

b) Preparation of a Stencil

An optical microscopy slide (26 mm×76 mm) is washed in a 1:1 solution of oxygenated water/sulfuric acid for 20 minutes. 1 nm of titanium and then 9 nm of chromium are deposited on this slide, using a Plassys type electron gun evaporator. An AZ1512HS type resin (available from Clariant) diluted to 50% in its AZ-EB solvent (which is a propyleneglycolmonomethylether acetate solvent) is deposited on the chrome-plated side of the slide using a whirler, as a result of which a resin thickness of 600 nm is obtained. It is annealed for 2 minutes at 120° C. It is illuminated through a Sodalime stencil with the required pattern for 2 seconds (MJB4 aligner at 30 mW/cm$^2$). After development (AZ-Developer+de-ionized water 1:1, 1 minute), the slide is rinsed intensively with de-ionized water.

The slide is then placed in a DPS type etching reactor and is etched for 30 seconds using a chlorine treatment (⅔Cl$_2$: ⅓O$_2$) at a pressure of between 10 and 25 mTorrs. The resin is removed by an O$_2$ plasma for 30 seconds in the DPS reactor. The slide is then made hydrophobic by an Optool treatment (Daikin DSX): immersion for 1 minute in Optool diluted to 1:1000 in perfluorohexane. The slide is then left for 1 hour in steam at 80° C. It is finally immersed in perfluorohexane for 10 minutes while stirring slowly.

Figure 3:
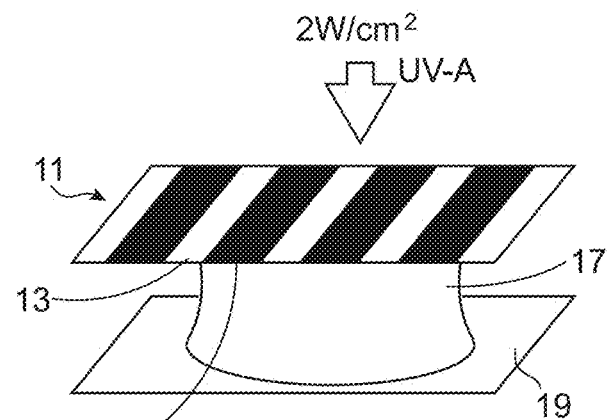
FIG. 3 shows a view of the device used for example 2.

The stencil is shown in FIG. 3 as reference 11, this stencil including an alternation between transparent zones 13 (not covered with titanium and chromium) consisting of 10 µm wide lines and zones 15 consisting of 40 µm wide lines covered with a 10 nm thick layer (1 nm of titanium and 9 nm of chromium) (these zones possibly being qualified as grey level zones).

This stencil will be inserted between a light flux (shown by an arrow in the figure indicating that it is a UV-A flux at 2 W/cm$^2$) and the solution (shown as reference 17) deposited on the glass slide 19 mentioned above and that will be photocrosslinked to form the target matrix, namely a matrix with contiguous zones with a distinct stiffness, namely 10 µm wide lines alternating with 40 µm wide lines.

c) Preparation of the Hydrogel Matrix

The hydrogel matrix is prepared in the same way as in example 1 described above.

The stiffness of the matrix obtained was determined.

This was done by measuring the local stiffness of the gel using an atomic force microscope in an aqueous medium (brand JPK). The resistance of the gel to penetration of the point is recorded. A 100 µm scan is made from the centre of the network of lines spaced at 40 µm. The scans are made at a pitch of 5 µm. The result is a series of indentation curves. Each curve is processed using the manufacturer's protocol with an elastic indentation model. Each point of the graph is obtained by taking the average of the measurements on two curves.

Figure 4:
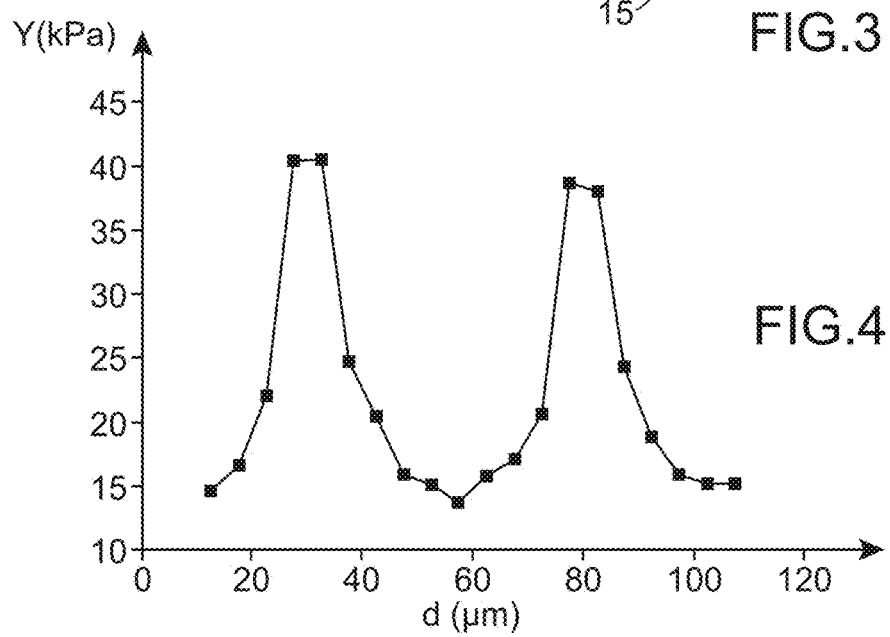
FIG. 4 shows a chart illustrating the variation of the stiffness Y (in kPa) of the matrix obtained for example 2 as a function of the distance d (in µm).

The results are shown in FIG. 4 representing the variation of the stiffness Y (in kPa) as a function of a distance d (in µm). Abscissa point 0 corresponds approximately to the centre of the network.

The shape of the curve confirms the presence of stiffness channels at a separation of about 40 µm, these stiffness channels corresponding to the zones illuminated through transparent zones in the above-mentioned stencil.

A cell culture was also made on the matrices mentioned above.

Before starting, the matrix was functionalized with fibronectin. This was done by gluing the 30 mm diameter cover glass on which the hydrogel is polymerized to the bottom of a Petri dish in which a 35 mm diameter hole is drilled. Water is drawn out of the dish, 1 mg of Sulfo SDA (Pierce) (corresponding to succinimidyl-ester diazirine) is dissolved in 2.27 mL of sterile de-ionized water. The solution obtained is deposited on the matrix and is left for 2 hours in the dark. After this time, it is drawn in with the pipette and 2 mL of a 25 mg/mL fibronectin solution in sterile PBS is deposited for 1 hour. The dish is always kept in the dark. This solution is drawn in with the pipette and the dish is placed under the Eleco UVP281 lamp (2 W/cm$^2$) for 3 min. The matrix is rinsed 3 times with sterile PBS (phosphate buffer salt).

LN229 cells (glioblastoma tumor cells extracted from the right parieto-occipital frontal cortex) are seeded at a density of 5000 cells/cm$^2$ in a DMEM medium (Eagle minimum essential medium modified by Dubelcco) to which 10% FBS and 1% ATAM are added.

Figure 5:
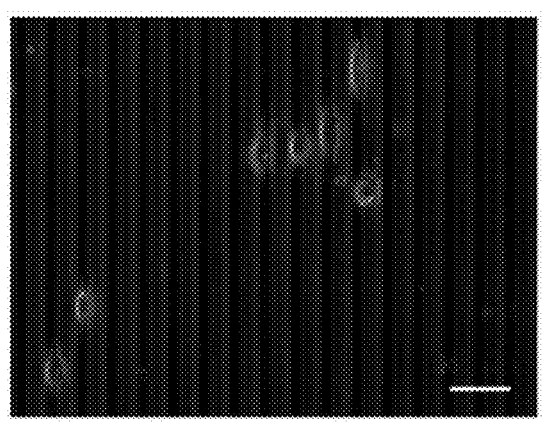
FIG. 5 shows a photograph of the matrix obtained for example 2 after cell seeding.

As can be seen in FIG. 5, that is a photograph made by phase contrast microscopy with magnification 20× on an inverted microscope 2 hours after seeding, there is a concentration of cells along the zones illuminated through transparent zones of the stencil, these zones corresponding to rigid zones (and corresponding to the above-mentioned stiffness channels).

Example 3

This example illustrates preparation of a matrix comprising different stiffness zones involving the following steps:
a step to prepare a glass cover glass that will be used as a support for the matrix (a);
a step in which a stencil is prepared (b);
a step in which the hydrogel matrix is prepared (c).

a) Preparation of the Cover Glass

The cover glass is prepared in the same way as in example 1 described above.

b) Preparation of a Stencil

An optical microscopy slide (26 mm×76 mm) is washed in a 1:1 solution of oxygenated water/sulfuric acid for 20 minutes. On this slide, an AZ1512HS type resin (available from Clariant) is deposited using a whirler at a rate of 2500 revolutions/min for 120 seconds. It is annealed for 2 minutes at 100° C. It is illuminated for 35 seconds with a 6 mW/cm$^2$ UV lamp filtered on the 365 nm wavelength through a PDF stencil printed on a transparency and having a 100 µm wide black line. The pattern is developed using the AZ-EBR developer for 30 seconds. After development, the cover glass is once again annealed for 2 minutes at 120° C. 1 nm of titanium and then 4 nm of chromium are deposited using a Plassys type electron gun evaporator. The cover glass is then immersed for 1 minute in acetone to remove the resin line. The result is a 100 µm channel transparent to the medium of the chrome-plated cover glass.

The cover glass is then made hydrophobic by an Optool treatment (Daikin DSX): immersion for 1 minute in Optool diluted to 1:1000 in perfluorohexane. The cover glass is then left for 1 hour in steam at 80° C. It is finally immersed in perfluorohexane for 10 minutes while stirring slowly.

Figure 6:
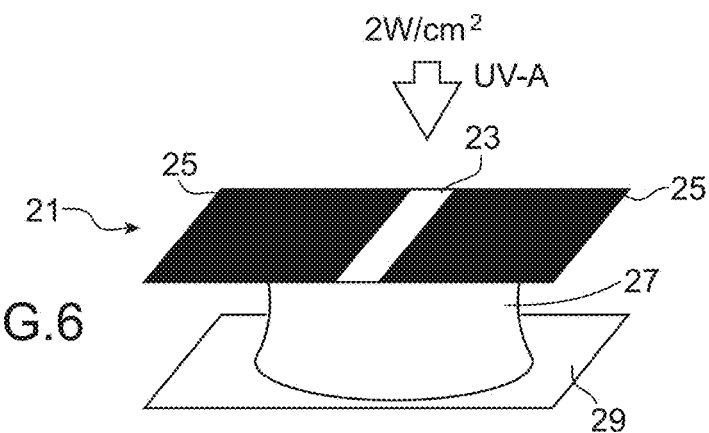
FIG. 6 shows a view of the device used for example 3.

The stencil obtained is shown in FIG. 6 as reference 21, this stencil comprising a transparent zone 23 (not covered with titanium and chromium) consisting of a 100 µm wide line and two zones 25 surrounding the zone 23, these two zones being covered by a 5 nm thick layer (1 nm titanium and 4 nm chromium) (these zones possibly being qualified as grey level zones).

This stencil will subsequently be inserted between a light flux (shown by an arrow in the figure indicating that it is a UV-A flux at 2 W/cm$^2$) and the solution (shown as reference 27) deposited on the above-mentioned cover glass 29 and that will be photocrosslinked in order to form the target matrix, namely a matrix with contiguous zones with a distinct stiffness, namely in this case a central rigid zone surrounded by two soft end zones.

c) Preparation of the Hydrogel Matrix

The hydrogel matrix is prepared in the same was as in example 1 described above, except that the illumination duration is only 8 s.

The stiffness of the matrix obtained was determined.

This was done by measuring the local stiffness of the gel using an atomic force microscope in an aqueous medium (brand JPK). The resistance of the gel to penetration of the point is recorded. A 200 µm scan is made through the channel. The scans are made at a pitch of 10 µm. The result is a series of indentation curves. Each curve is processed using the manufacturer's protocol with an elastic indentation model. Each point on the graph is obtained by taking the average of two measurements made on two separate points at a distance of 10 µm parallel to the channel.

Figure 7:
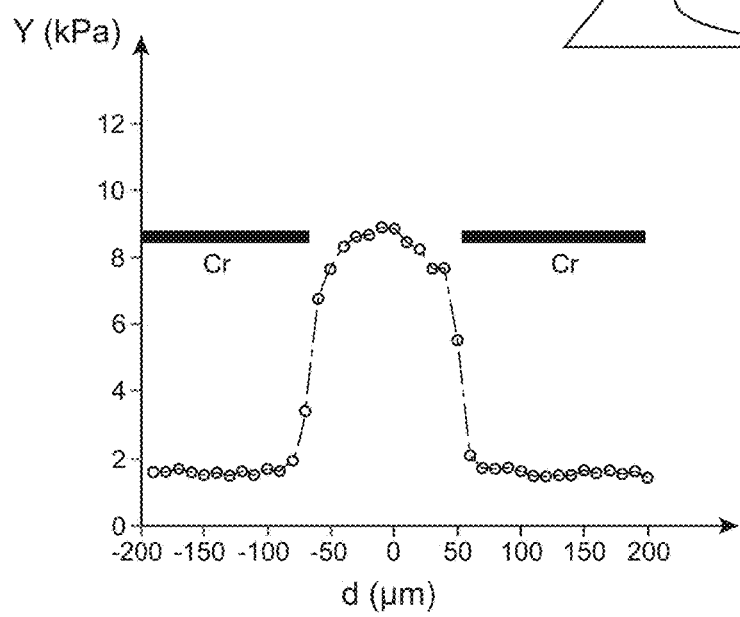
FIG. 7 shows a chart illustrating the variation of the stiffness Y (in kPa) of the matrix obtained in example 3 as a function of a distance d (in µm) relative to the centre of the channel of this matrix (this distance to the centre being equal to 0 at the abscissa).

The results are shown in FIG. 7 representing the variation of the stiffness Y (in kPa) as a function of a distance d (in µm) from the centre of the channel (the value of this distance at the centre being equal to 0 at the abscissa).

Considering the shape of the curve, it can be seen that there is a stiffness channel corresponding to the zone illuminated through the transparent zone of the stencil.

A cell culture was also made on the matrices obtained above.

Preferably, the matrix is functionalized with fibronectin. This was done by gluing the 30 mm diameter cover glass on which the hydrogel is polymerized to the bottom of a Petri dish in which a 35 mm diameter hole is drilled. Water is drawn out of the dish, 1 mg of Sulfo SDA (Pierce) (corresponding to succinimidyl-ester diazirine) is dissolved in 2.27 mL of sterile de-ionized water. The solution obtained is deposited on the matrix and is left for 2 hours in the dark. After this time, it is drawn in with the pipette and 2 mL of a 25 mg/mL fibronectin solution in sterile PBS is deposited for 1 hour. The dish is always kept in the dark. This solution is drawn in with the pipette and the dish is placed under the Eleco UVP281 lamp (2 W/cm$^2$) for 3 min. The matrix is rinsed 3 times with sterile PBS.

Hela cells (immortal cells extracted from a malignant tumor of the cervix of the uterus) are seeded at a density of 5000 cells/cm$^2$ in a DMEM medium to which 10% FBS and 1% ATAM are added.

Figure 8:
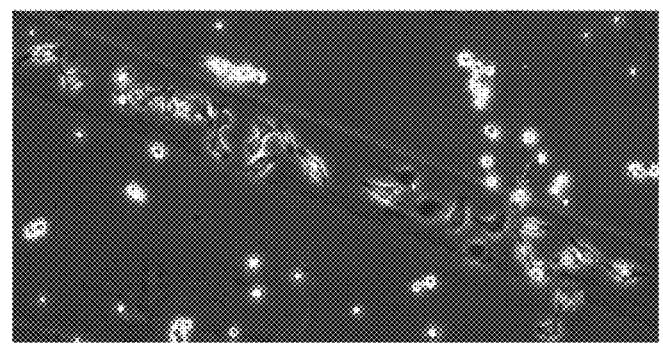
FIG. 8 shows a photograph of the matrix obtained for example 3 after cell seeding.

As can be seen in FIG. 8 that is a photograph made by phase contrast microscopy at a magnification of 20× on an inverted microscope 2 hours after seeding, there is a concentration of cells along the above-mentioned channel, this channel corresponding to the zone in the matrix with the highest stiffness.

Example 4

This example illustrates the preparation of a matrix comprising zones with different stiffnesses in the form of a first network of 6 µm wide lines alternating with 2 µm wide lines and a second network of 4 µm wide lines alternating with 2 µm wide lines involving the following steps:
- a step to prepare a glass cover glass that will be used as a support for the matrix (a);
- a step in which a stencil is prepared (b);
- a step in which the hydrogel matrix is prepared (c).

a) Preparation of the Cover Glass

The cover glass is prepared in the same way as in example 1 described above.

b) Preparation of a Stencil

An optical microscopy slide (26 mm×76 mm) is cleaned in a 1:1 solution of oxygenated water/sulfuric acid for 20 minutes. 1 nm of titanium and then 4 nm of chromium are deposited on this cover glass, using a Plassys type electron gun evaporator. An AZ1512HS type resin (available from Clariant) diluted to 50% in its AZ-EBR solvent (which is a propyleneglycolmonomethylether acetate solvent) is deposited on the chrome-plated side of the slide using a whirler, as a result of which a resin thickness of 600 nm is obtained. It is annealed for 2 minutes at 120° C. It is illuminated through a Sodalime stencil with the required pattern for 2 seconds (MJB4 aligner at 30 mW/cm$^2$). After development (AZ-Developer+de-ionized water 1:1, 1 minute), the slide is rinsed intensively with de-ionized water.

The slide is then placed in a DPS type etching reactor and is etched for 30 seconds using a chlorine treatment (⅔Cl$_2$: ⅓O$_2$) at a pressure of between 10 and 25 mTorrs. The resin is removed by an O$_2$ plasma for 30 seconds in the DPS reactor. The slide is then made hydrophobic by an Optool treatment (Daikin DSX): immersion for 1 minute in Optool diluted to 1:1000 in perfluorohexane. The slide is then left for 1 hour in steam at 80° C. It is finally immersed in perfluorohexane for 10 minutes while stirring slowly.

Figure 9:
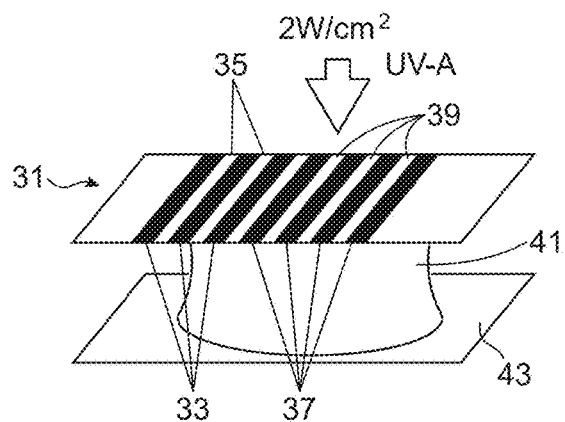
FIG. 9 shows a view of the device used for example 4.

The stencil is shown in FIG. 9 as reference 31, this stencil comprising a first network of covered 6 µm wide lines 33 (called grey level lines) alternating with 2 µm wide lines 35 (transparent lines) and a second network of covered 4 µm wide lines 37 (called grey level lines) alternating with 2 µm wide lines 39 (transparent lines, in other words not covered with titanium and chromium).

This stencil will be inserted between a light flux (shown by an arrow in the figure indicating that it is a UV-A flux at 2 W/cm$^2$) and the solution (shown as reference 41) deposited on the glass slide 43 mentioned above and that will be photocrosslinked to form the target matrix, namely a matrix with a first network of 6 µm wide lines (soft lines) alternating with 2 µm wide lines (stiff lines) and a second network of 4 µm wide lines (soft lines) alternating with 2 µm wide lines (stiff lines).

c) Preparation of the Hydrogel Matrix

The hydrogel matrix is prepared in the same way as in example 1 described above.

The stiffness of the matrix obtained was determined.

This was done by measuring the local stiffness of the gel using an atomic force microscope in an aqueous medium (brand JPK). The resistance of the gel to penetration of the point is recorded. A 30 µm scan is made from the centre of the network of lines spaced at 6 µm. In exactly the same way, a 20 µm scan is made from the centre of the network of lines at a spacing of 4 µm. The scans are made at a pitch of 1 µm. The result is a series of indentation curves. Each curve is processed using the manufacturer's protocol with an elastic indentation model. Each point on the graph is the average of two measurements made on two points at a distance of 10 µm parallel to the lines.

Figure 10:
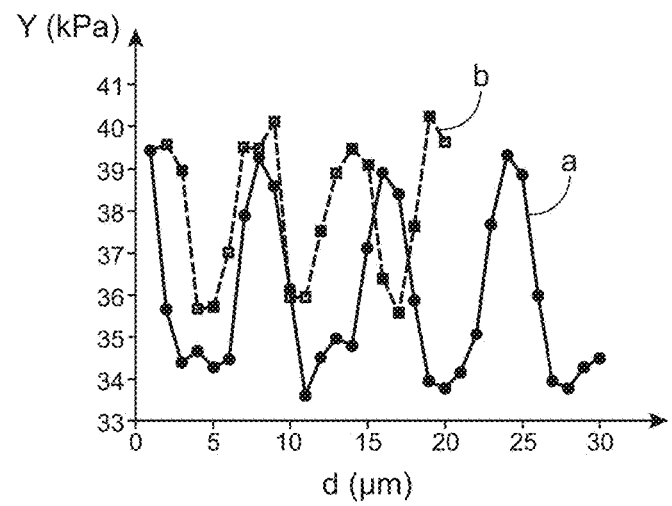
FIG. 10 shows a chart illustrating the variation of the stiffness Y (in kPa) of the matrix obtained for example 4 as a function of the distance d (in µm).

The results are shown in FIG. 10 representing the variation of the stiffness Y (in kPa) as a function of a distance d (in µm). The origin d=0 on each curve corresponds to the centers of the networks of lines spaced at 4 µm (grey dashed lines) and 6 µm (continuous black line) respectively. Two curves are shown: one curve a) for the first network of lines (alternation of soft 6 µm lines alternating with 2 µm rigid lines) and a curve b (alternation of 4 µm soft lines alternating with 2 µm rigid lines).

Figure 11:
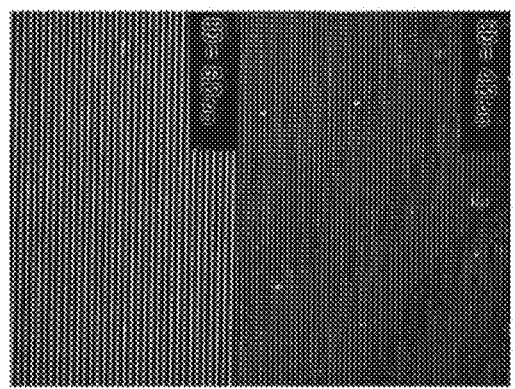
FIG. 11 shows a photograph of a top view of the matrix obtained for example 4.

The shape of these two curves confirms the presence of stiffness channels located at the rigid lines, these stiffness channels being at a spacing of 6 µm (curve a) or 4 µm (curve b), the stiffness gradient being very steep particularly for the first network of lines between rigid lines and soft lines, this arrangement being confirmed by FIG. 11 that shows a photograph of the matrix obtained seen from above.

Example 5

This example illustrates the preparation of a hydrogel matrix comprising zones with distinct stiffness comprising the following patterns from left to right respectively:
- two adjacent lines each comprising three patterns in the shape of anchors
- two adjacent lines each comprising three patterns in the shape of triangles; and
- two adjacent lines each comprising three patterns in the form of dunce caps, said method including the following steps:
a step to prepare a cover glass that will act as a support for the hydrogel matrix (a);
a step in which a stencil is prepared (b);
a step in which the hydrogel matrix is prepared (c).

a) Preparation of the Cover Glass

The cover glass is prepared in the same way as in example 1 described above.

b) Preparation of a Stencil

An optical microscopy slide (26 mm×76 mm) is washed in a 1:1 solution of oxygenated water/concentrated sulfuric acid for 20 minutes. 1 nm of titanium and then 9 nm of chromium are deposited on this slide using a Plassys type electron gun evaporator. An AZ1512HS type resin (available from Clariant) diluted to 50% in its AZ-EBR solvent (which is a propyleneglycolmonomethylether acetate solvent) is deposited on the chrome-plated side of the slide using a whirler turning at 3000 rpm for 30 seconds, as a result of which a resin thickness of 600 nm is obtained. It is illuminated through a Sodalime stencil with the required patterns. After development, the slide is placed in a DPS type etching reactor and is etched for 30 seconds using a chlorine treatment ($\frac{2}{3}Cl_2$:$\frac{1}{3}O_2$) at a pressure of between 10 and 25 mTorrs. The resin is removed by an $O_2$ plasma for 30 seconds in the DPS reactor. The slide is then made hydrophobic by an Optool treatment (Daikin DSX): immersion for 1 minute in Optool diluted to 1:1000 in perfluorohexane. The slide is then left for 1 hour in steam at 80° C. It is finally immersed in perfluorohexane for 10 minutes while stirring slowly.

Figure 12:
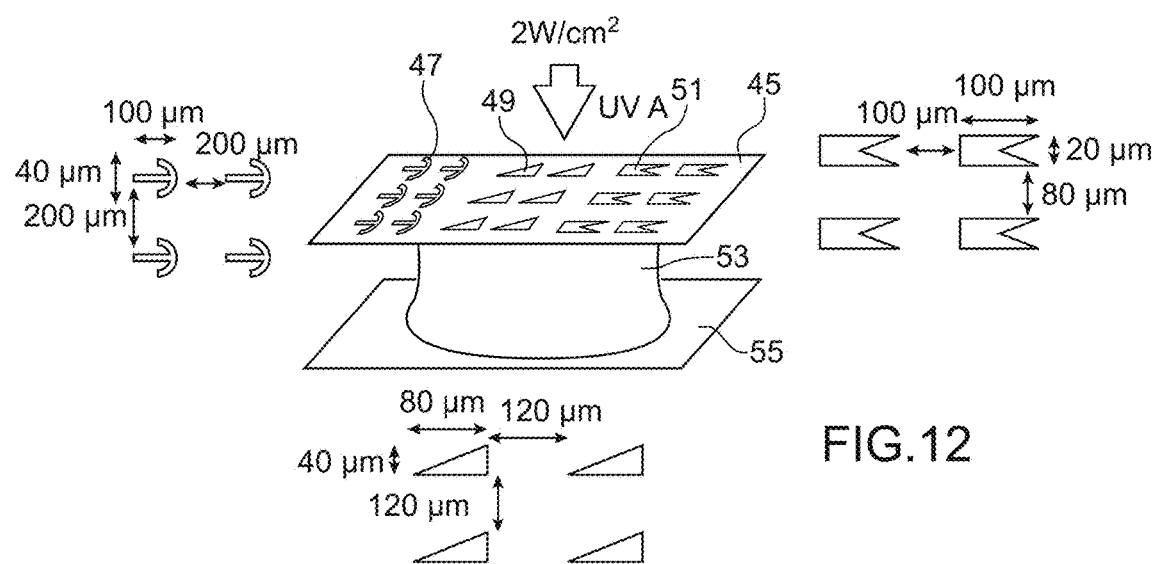
FIG. 12 shows a view of the device used for example 5.

The stencil is shown in FIG. 12 as reference 45, this stencil comprising from left to right, a first network of lines 47 each comprising three anchor shaped patterns (the dimensions and spacing of which are shown to the left of the stencil), a second network of lines 49 each comprising three right-angled triangle shaped patterns (the dimensions and spacing of which are shown in the lower part of the figure) and a third network of lines 51 each comprising three dunce cap shaped patterns (the dimensions and spacing of which are shown to the right of the stencil), the patterns in the first network, the second network and the third network being transparent, in other words not covered with titanium and chromium.

This stencil will be inserted between a light flux (shown by an arrow on the figure indicating that it is a UV-A flux at 2 W/cm$^2$) and the solution (shown as reference 53) deposited on the above-mentioned slide 55 that will be photocrosslinked in order to form the target matrix, namely a matrix with a first network of lines each comprising three anchor shaped patterns, a second network of lines each comprising three right angle triangle shaped patterns and a third network of lines each comprising three dunce cap shaped patterns.

c) Preparation of the Hydrogel Matrix

The hydrogel matrix is prepared in the same way as in example 1 described above.

A cell culture was prepared on the matrices described above.

REF52 cells were seeded uniformly on the above-mentioned matrix at a cell density of 5000 cells/cm$^2$. Two hours after seeding, the cells were fixed using paraformaldehyde (PAF) at 4% containing 0.5% of triton for 10 minutes and then with PAF at 4% for 20 minutes. Actin is marked with phalloidin-Cy5 on the cells thus fixed and permeabilized, vinculin is marked with a monoclonal anti-vinculin antibody and then with a mouse anti-IdG antibody coupled with Alexa 488, while the nuclei are marked with Hoechst stain. After these fluorescent markings, cells are observed in phase contrast and fluorescence microscopy using a *60 lens on an inverted microscope.

Figure 13:
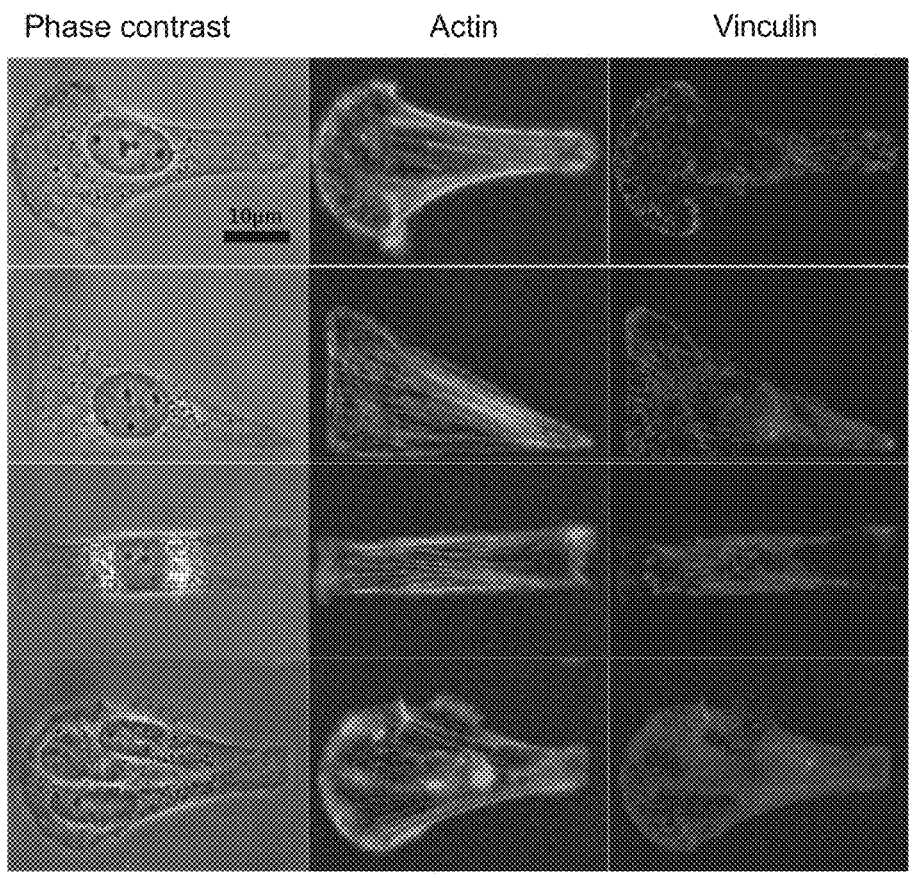
FIG. 13 is a photograph illustrating the cell positioning phenomenon with conformation of the cell geometry with the geometry of the pattern with higher stiffness than the zones surrounding this pattern, in accordance with example 5.

As shown in FIG. 13, the cells are localized on the above-mentioned patterns with the highest stiffness (in other words the anchor, right-angle triangle and dunce cap shaped patterns).

Example 6

This example illustrates the preparation of a hydrogel matrix comprising zones with distinct stiffness with a network of 2 μm diameter pads at a spacing of 6 μm or a network of 5 μm diameter pads at a spacing of 7.5 μm, these pads having a stiffness of 15 kPa, while the space between the pads is composed of a soft matrix with a stiffness of 6 kPa.

a) Preparation of the Cover Glass

The cover glass is prepared in the same way as in example 1 described above.

b) Preparation of a Stencil

The stencil is prepared in the same way as in the examples described above.

c) Preparation of the Hydrogel Matrix

The hydrogel matrix is prepared in the same way as in the previous examples.

A cell culture was made on the matrices obtained above.

REF52 cells overexpressing paxiline coupled to YFP (symbolized as REF52-Pax-YFP) were seeded uniformly on the above-mentioned matrix at a cell density of 5000 cells/cm$^2$. Two hours after seeding, the cells were fixed using paraformaldehyde (PAF) at 4% containing 0.5% triton for 10 minutes and then with PAF at 4% for 20 minutes. Actin is marked with phalloidin-Cy5 on the cells thus fixed and permeabilized, vinculin is marked with a monoclonal anti-vinculin antibody and then with a mouse anti-IdG antibody coupled with Alexa 488, while the nuclei are marked with Hoechst stain. After these fluorescent markings, cells are observed in phase contrast and fluorescence microscopy using a *60 lens on an inverted microscope.

Figure 14:
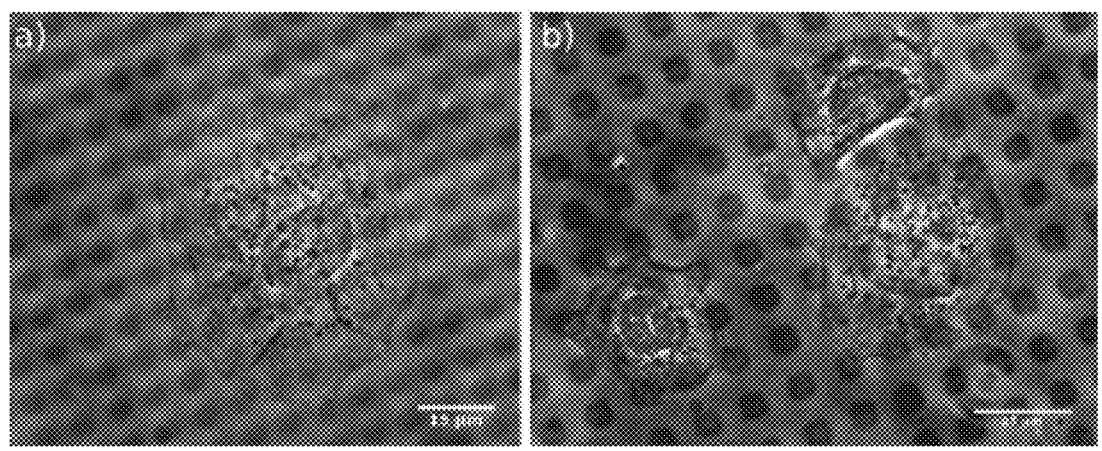
FIG. 14 shows two enlarged views (a and b) of the matrix seen from above after cell seeding for example 6.

As shown in FIG. 14 illustrating an enlarged view of the matrices (part (a) for the matrix with 2 μm diameter pads or part (b) for the matrix with 5 μm diameter pads), the adhesion of cells takes place at focal contacts at which vinculin is collected, these focal contacts being produced only on the rigid pads (in other words the zones with the highest stiffness). When the distance between the pads increases, the cellular shape becomes increasingly constrained by the position of the focal contacts.

Example 7

This example 7 is a variant of example 6 described above under similar conditions, except that the matrix contains pads with a stiffness of 12 kPa and a diameter of 6 μm, these pads being at a spacing of 9 μm, the space between the pads being composed of a soft matrix with a stiffness of 4 kPa.

Figure 15:
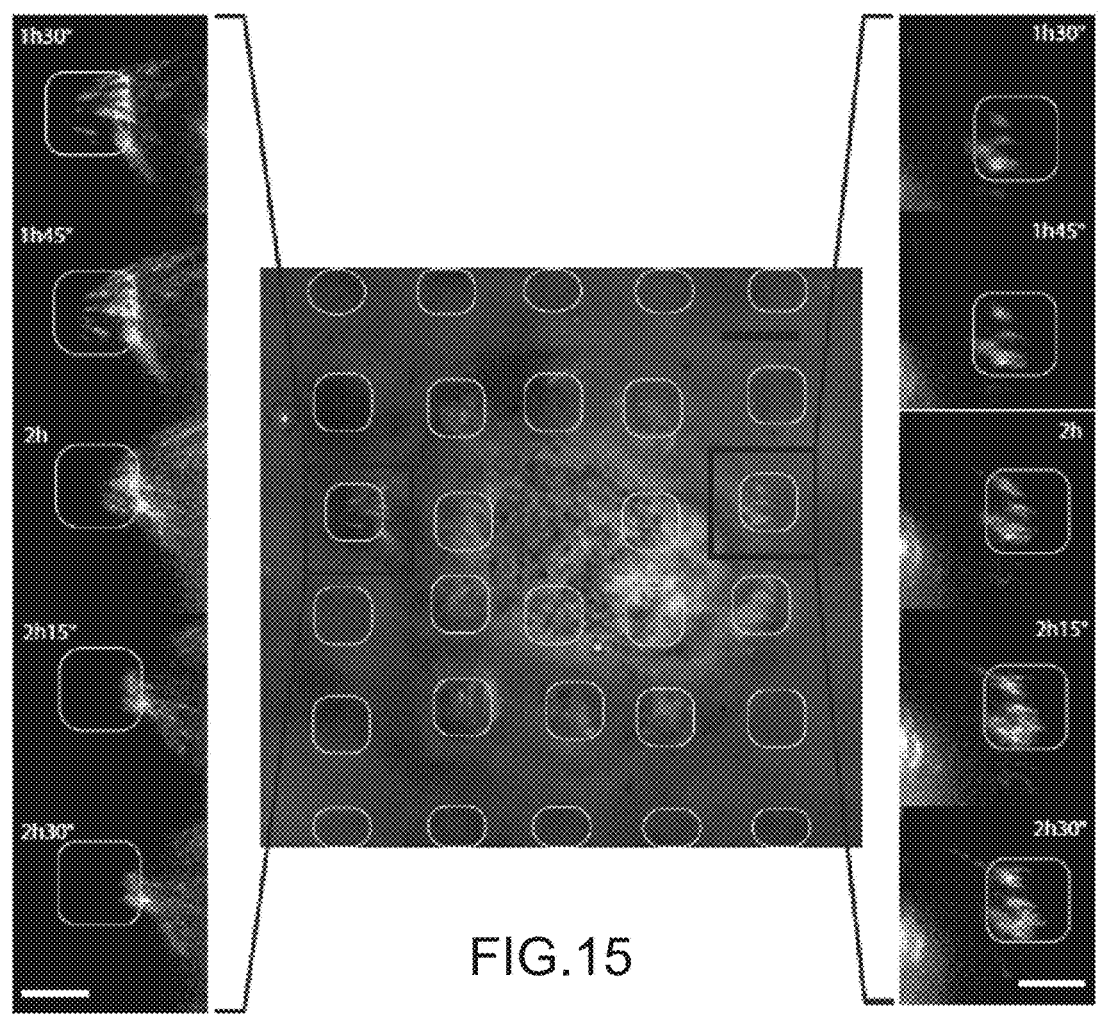
FIG. 15 shows an enlarged view (with right and left inserts taken at different cell seeding durations) of the matrix seen from above after cell seeding for example 7.

Images were taken every fifteen minutes as shown in FIG. 15 attached in the appendix. The adhesion of cells takes place at focal contacts that are set up only at the rigid pads at which paxiline-YFP collects.

The left and right inserts show how the two focal contacts change with time. The focal contact in the left insert disintegrates progressively, while the focal contact in the right insert is reinforced. These effects result in a cellular migration from the left towards the right.

Example 8

This example is aimed at highlighting the modulation of the cell shape by varying the spacing of rigid pads.

It forms a variant of example 6 mentioned above and performed under similar conditions, except that the matrix comprises pads with a stiffness of 6 kPa and a diameter of 10 μm, these pads being at a spacing of 10 μm, the space between the pads being composed of a soft matrix with a stiffness of 1 kPa (stiffness value less than the cell survival threshold).

Figure 16:
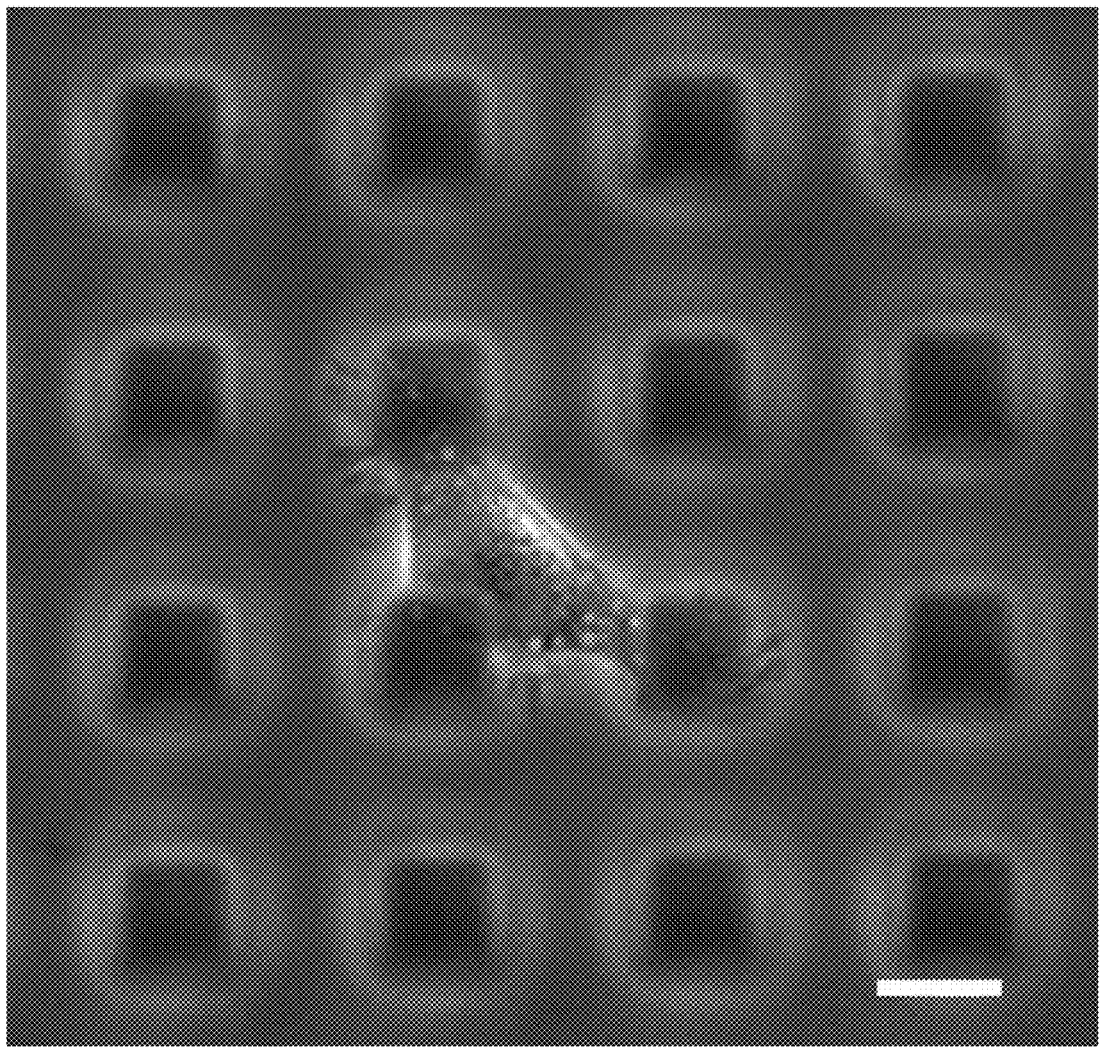
FIG. 16 shows an enlarged view of the matrix seen from above after cell seeding for example 8.

As shown in FIG. 16, a REF52 cell has a triangular shape defined by the distribution of pads. Note that only the cells that were directly deposited on the patterns or were at a distance less than the cell size (of the order of 10 μm) survived and got organized on the rigid pads.

Example 9

This example forms a variant of example 6 mentioned above performed under similar conditions, except that the matrix comprises pads with a stiffness of 15 kPa and a diameter of 3 μm, these pads being at a spacing of 1 μm, the space between the pads consisting of a soft matrix with a stiffness of 5 kPa.

Figure 17:
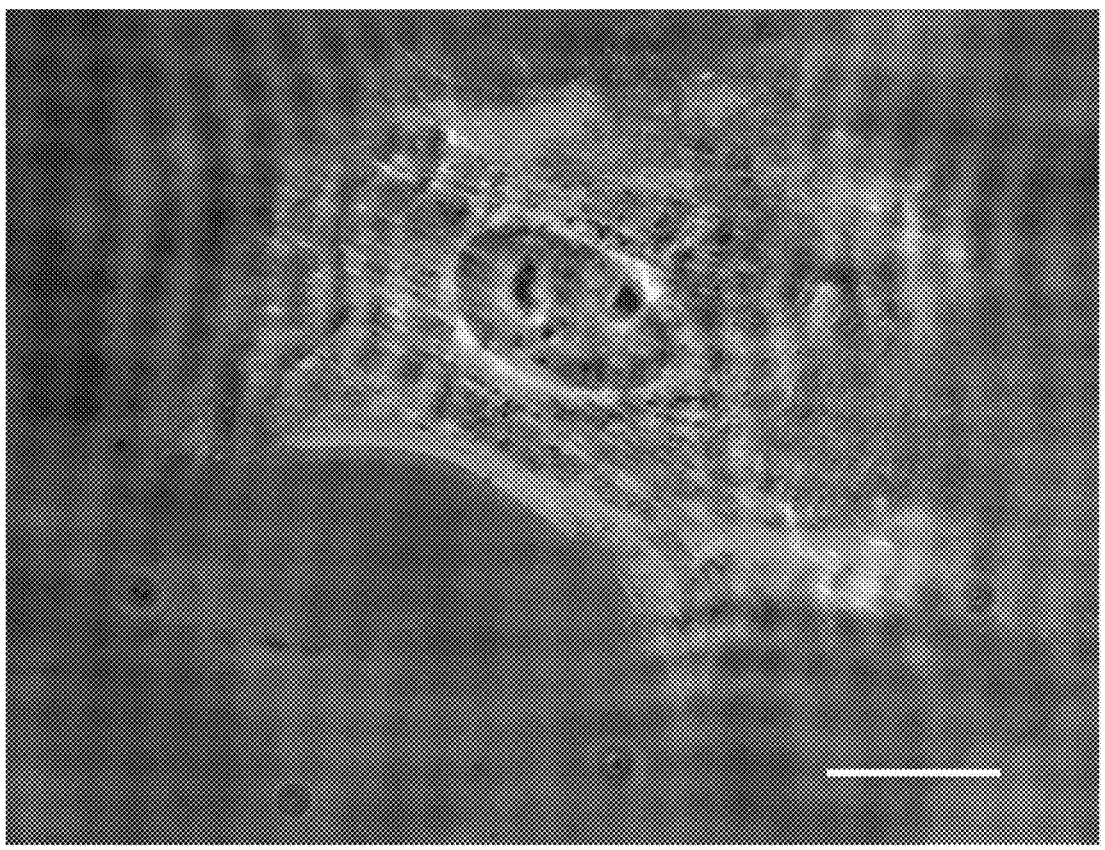
FIG. 17 shows an enlarged view of the matrix seen from above after cell seeding for example 9.

As shown in FIG. 17, the cell shape is completely deformed.

It can be deduced from examples 7 to 9 mentioned above that illustrate matrices with rigid patterns with a size smaller than the cell size, that the pattern size limits the growth of adhesive sites and the pattern density influences the cell geometry. Consequently, the choice of the size and spacing of patterns influence firstly the geometry of the cell and secondly contractile forces applied by the cell.

The invention claimed is:

1. A method for preparing a hydrogel type matrix comprising at least two contiguous zones with distinct stiffnesses comprising
  photopolymerizing a solution in the presence of a polymerization catalyst, said solution comprising one or several polymerizable compounds and a photopolymerization initiator, by applying light onto the entire solution and at a different intensity in at least two zones of the solution, thereby obtaining a hydrogel matrix comprising at least two contiguous zones with distinct stiffnesses.

2. A method according to claim 1, wherein the hydrogel type matrix is made from a material selected from the group consisting of:
  polyacrylamides;
    polyethyleneglycols containing repetitive patterns derived from polymerization of acrylate or methacrylate compounds;
    polysaccharides, optionally modified;
    (co)polymers derived from polymerization of diacrylate and/or (meth)acrylate compounds;
    polyvinyl alcohols containing repetitive patterns derived from polymerization of acrylate or methacrylate compounds;
    dextranes containing repetitive patterns derived from polymerization of (meth)acrylate compounds;
    polypropylene fumarates and derivatives thereof; and combinations thereof.

3. A method according to claim 1, wherein the photopolymerization initiator is selected from the group consisting of aromatic ketones, acridine compounds and fluorone compounds.

4. A method according to claim 1, wherein the polymerization catalyst is an amine compound.

5. A method according to claim 1, wherein the solution further comprises one or several ingredients selected from the group consisting of stains, cross-linking agents, water and mixtures thereof.

6. A method according to claim 1, wherein light is applied to the solution through a stencil, delimiting zones with distinct light intensity.

7. A method according to claim 1, wherein light is applied according to a distribution with spatially modulated intensity.

8. A method according to claim 1, wherein the hydrogel type matrix comprises at least two contiguous zones with distinct stiffnesses with a stiffness gradient of the order of 1 kPa/μm.

9. A method according to claim 1, further comprising a matrix functionalization step after the photopolymerizing, using a protein inducing cell adhesion through integrins.

10. An in vitro cell adhesion method comprising:
  a) preparing a hydrogel type matrix according to claim 1;
  b) depositing cells of one or several types on the matrix obtained in step a), such that the cells of at least one of the types adhere entirely or partly to some zones of the matrix with higher stiffness than contiguous zones.

11. An in vitro cell shaping method comprising:
  a) preparing a hydrogel type matrix according to claim 1;
  b) depositing cells of one or several types on the matrix obtained in step a), such that the cells of at least one of the types are concentrated entirely or partly on some zones of the matrix with higher stiffness than contiguous zones and adopt the shape of said higher stiffness zones.

12. A method for preparing a hydrogel type matrix comprising at least two contiguous zones with distinct stiffnesses comprising photopolymerizing a solution in the presence of a polymerization catalyst, said solution comprising one or several polymerizable compounds and a photopolymerization initiator, by application of light onto the entire solution and at a different intensity in at least two zones of the solution, wherein a hydrogel matrix is obtained comprising at least two contiguous zones with distinct stiffnesses and, wherein the solution comprises acrylamide, a photopolymerization initiator with the following formula:

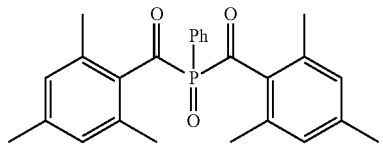

where Ph denotes a phenyl group,
n-propylamine as the polymerization catalyst, N,N'-methylenebisacrylamide as the cross-linking agent and water.

* * * * *